United States Patent [19]

Thomas

[11] 3,946,056

[45] Mar. 23, 1976

[54] METHOD FOR PRODUCING STANNIC TERTIARY ALKOXIDE

[75] Inventor: Ian M. Thomas, Temperance, Mich.

[73] Assignee: Owens-Illinois, Inc., Toledo, Ohio

[22] Filed: July 26, 1974

[21] Appl. No.: 492,351

[52] U.S. Cl. .......................................... 260/429.7
[51] Int. Cl.² .......................................... C07F 7/22
[58] Field of Search ................................ 260/429.7

[56] References Cited
UNITED STATES PATENTS

| | | | |
|---|---|---|---|
| 2,269,498 | 1/1942 | Wainer | 260/429,7 X |
| 2,626,953 | 1/1953 | Mack | 260/429.7 |
| 2,684,972 | 1/1954 | Haslam | 260/429 |
| 2,745,820 | 5/1956 | Mack | 260/429.7 X |
| 3,772,355 | 11/1973 | Merz | 260/429 R |

OTHER PUBLICATIONS

Bradley, Progress In Inorganic Chemistry, Vol. 2, Interscience Pub. Inc. N.Y. pp. 303–314 (1960).

*Primary Examiner*—Helen M. S. Sneed
*Attorney, Agent, or Firm*—Robert F. Rywalski; Edward J. Holler

[57] ABSTRACT

A method is disclosed for forming stannic tetra-(tertiary-alkoxides) wherein the alkoxide groups contain from 4 to 8 carbon atoms, which process includes starting with a tin tetrahalide and involves reactions with an alkylamine and a tertiary alcohol. The resulting products are volatile tin compounds and find utility as a source of tin oxide. For example, the compounds may be hydrolyzed with water and then pyrolyzed to provide a source of ultra high purity tin oxide.

21 Claims, No Drawings

METHOD FOR PRODUCING STANNIC TERTIARY ALKOXIDE

FIELD OF THE INVENTION

The present invention is directed to the formation of tin compounds and, more particularly, is directed to the formation of tin compounds of the formula $Sn(OR)_4$ wherein R is a tertiary alkyl group containing from 4 to about 8 carbon atoms.

BACKGROUND OF THE ART OF SYNTHESIZING TIN ALKOXIDES

As a general matter, certain metal alkoxides have been widely prepared in the past by a process which involves the use of metal halides, alcohols, and ammonia as reagents. The ammonia was employed to force complete substitution of halide and to scavenge the by-product hydrohalide, e.g. HCl, so as to remove it in the form of ammonium chloride. This removal of the HCl is important because of the side reaction between, for example, HCl and an alcohol taking place which would result in the formation of water and hence would undesirably hydrolyze the desired alkoxide product. In the case of forming a tertiary alkoxide the ammonia method is generally not satisfactory because the tertiary alcohols react quite rapidly with the HCl and the ammonia is not capable of removing the HCl effectively. The use of amines has also been described but not for tin.

Bradley, et al. (*Chemical Society Journal*, 1957, Part IV, page 4775 et seq. entitled, "The Preparation and Properties of Stannic Alkoxides") begin with the statement that "little is known about stannic alkoxides". In this article it is indicated, that in view of the successful preparation of alkoxides of titanium, germanium, zirconium, and hafnium through the tetrahalide, alcohol and ammonia method, they attempted to make pure stannic alkoxides from stannic chloride. It is indicated that the method did not yield pure stannic alkoxide. Success was obtained, however, in producing stannic tetra(tertiary-alkoxides) by an alcohol interchange process from tin ethoxide, the latter being prepared by the use of sodium ethoxide as a reactant. This technique, however, is a rather prolonged stepwise process and would not be economically justified.

In the *Canadian Journal of Chemistry*, Volume 39 (1961), page 1386 et seq., it is indicated by the present inventor that alkoxides may be prepared by reacting an alcohol with compounds having metal-nitrogen bonds, that is, compounds of the formula $M(NR_2)_x$ wherein M may, for example, be tin. The metal-nitrogen compounds are prepared by a reaction involving lithium diethylamide and those skilled in the art will readily appreciate the undesirable features of using such lithium compounds.

U.S. Pat. No. 2,269,498 indicates that amine compounds of Group IV metals can be produced by reacting a metal tetrahalide with an amine in an anhydrous solvent. While no tertiary alcohols are described as the solvent, in those instances where methanol is employed it may be that an alkoxide and an amine hydrochloride are formed, at least, as an intermediate product. This patent, however, has no recognition of a method for forming tin tetra(tertiary-alkoxides). Subject to this same deficiency in U.S. Pat. No. 2,901,452, wherein it is indicated that tin halide can be reacted with dimethylethanolamine and then treated with water and propylene or ethylene glycol.

U.S. Pat. No. 2,684,972 indicates difficulties in the art with regard to forming metal tertiary alkoxides, or metal esters of tertiary alcohols, and focuses on forming such metal tertiary alkoxides. While no examples are given it is prophetically indicated that tin tertiary alkoxides could be formed by the two-step process disclosed therein. In column 8 of this patent, it is indicated that the method of that patent eliminates the use of expensive organic amines such as pyridine. Presumably this statement contemplates the elimination of the combined use of pyridine and ammonia as set forth in the *Nature* article disclosed in column 1 thereof. The process of this patent, however, is not suitable for purposes of the present application, as will be seen by reference to the examples herein.

*Chemical Abstracts*, Volume 61 (33-Aliphatic Compounds) 1451E, entitled "Preparation of Stannic Ethoxide", discloses a process wherein stannic tetrachloride, ammonia, and ethyl alcohol is employed. There is no indication in that abstract of a technique for producing stannic tetra(tertiary-alkoxides) however.

THE INVENTION

In accordance with one feature of this invention there is provided a novel and simple process for the formation of tin tetra(tertiary-alkoxides), or compounds of the formula $Sn(OR)_4$ wherein R is a tertiary alkyl group having from 4 to 8 carbon atoms. According to another feature of this invention, there is provided an economical and expedient method for forming tin tetra(tertiary-alkoxides) wherein a problem in the prior art of scavenging halide, e.g. chloride, moieties from a starting metal tetrahalide is solved by deactivating the halide moiety by a reaction between an alkylamine and a stannic halide, which results in the formation of a stannic halide-alkylamine reaction product; this alkylamine-stannic halide reaction product is then reacted with a tertiary alcohol which results in the formation of the desired stannic tetra(tertiary-alkoxides). These alkoxides find many utilities which are known and readily apparent to those skilled in the art. One of the most interesting features of these compounds is, however, their relatively volatile nature, hence they provide a source for ultrahigh purity tin oxides. That is, the tin tetra(tertiary-alkoxides) as contemplated herein may be easily purified through evaporative techniques, for example, distillation, to provide an ultrahigh purity starting material which can then be hydrolyzed with water to form a hydrate thereof which upon pyrolysis forms ultrahigh purity tin oxide.

As used herein the term "alkylamine", either alone or, for example, in calling for the stannic halide-alkylamine reaction product contemplates conventional alkylamines and does not contemplate within its scope inorganic materials which by some might be thought to be amines; for example, that term does not comprehend ammonia within its scope nor compounds of the formula $M(NR_2)_x$ wherein R is an alkyl and x is an integer corresponding to the valence of the metal M, inasmuch as these latter materials are considered to be metal dialkylamides.

Thus, in accordance with one aspect of this invention there is provided a process for producing a compound for the formula $Sn(OR)_4$, wherein R is a tertiary-alkyl group containing from 4 to 8 carbon atoms, which process includes the steps of reacting a tertiary-alkyl alcohol, wherein the alkyl group contains from 4 to 8 carbon atoms with a stannic halide-alkylamine reaction product so as to form an amine hydrohalide byproduct and the tin compound indicated above, followed by a step of isolating the compound.

According to another aspect of this invention, there is provided a process for producing a stannic tetra(tertiary-alkoxide) which process includes the steps of reactively combining, at least a portion of at least a stoichiometric amount of an alkylamine, having up to 10 carbon atoms in each alkyl group thereof, with a stannic halide so as to form a reaction product thereof, and then adding to the reaction product a tertiary-alkyl alcohol having from 4 to 8 carbon atoms and reacting same so as to form an amine hydrohalide and the desired stannic tertiary alkoxide and wherein the remainder, if any, of the alkylamine reactant is added to the alkylamine-stannic halide reaction product substantially no later than the completion of the addition of the tertiary-alkyl alcohol; the desired product is then isolated by conventional techniques.

According to still another aspect of this invention, there is provided a process for forming a compound of the formula $Sn(OR)_4$, wherein R is a tertiary-alkyl group containing 4 to 8 carbon atoms, which process comprises reacting a stannic halide with a secondary or tertiary alkylamine in an anhydrous, inert, organic diluent wherein the amount of the amine is at least the stoichiometric amount, and preferably a stoichiometric excess, so as to form an alkylamine-stannic halide reaction product, which reaction product is then reacted with a tertiary alkyl alcohol, the amount of the tertiary alkyl alcohol being in a molar ratio to the stannic halide of at least about 4:1, so as to form an amine hydrohalide solid reaction product which is dispersed in a solution containing the desired tin tetra(tertiary-alkoxide) followed by the isolation of the desired compound.

According to still another aspect of this invention, a process is provided for producing tin tetra(tertiary-butoxide) or tin tetra(tertiary-pentoxide), i.e., tin tetra(tertiary-amyl oxide) using stannic tetrachloride, diethylamine and either tertiary pentanol or tertiary butanol with the amount of said pentanol or said butanol being in a molar ratio to said tin tetrachloride of about 4.05:1 to about 4.6:1 and with the amount of said diethylamine to said stannic tetrachloride being in the ratio of about 4.05:1 to about 4.6:1 which process comprises: reacting at least a portion of the diethylamine with the stannic chloride in the presence of an inert, anhydrous, organic diluent so as to form a reaction product and then adding said pentanol or said butanol to the reaction product and reacting same so as to form a dispersion of an amine hydrochloride in a solution containing the desired tin butoxide, or tin pentoxide, and wherein the remainder of the diethylamine, if any, is added to the reaction product substantially no later than the completion of the addition of the tertiary butanol or tertiary pentanol; the amine hydrochloride is then separated and the desired tin butoxide or tin pentoxide recovered. Thus, for example, if the amount of the amine which is first reacted is an amount sufficient to provide about 2 moles of diethylamine per moe of stannic chloride, the remainder which will be added at a later point in time will be at least about 2.05 moles of the diethylamine per mole of the starting tin tetrachloride.

As will be readily appreciated from the foregoing, the reagents employed in the process of this invention include stannic halides, preferably stannic tetrachloride, alkylamines, and tertiary alkyl alcohols. Most desirably and quite conveniently the reaction will, as indicated previously, be done in the presence of an anhydrous, inert, organic diluent. Exemplary of the alkylamines are those amines wherein the alkyl groups thereof have up to 10 carbon atoms, i.e., 1 to 10 carbon atoms and preferably wherein each alkyl group of the alkylamine contains 6 carbon atoms or less. Most desirably the alkyl groups of the alkylamine will contain 1 to 3 carbon atoms. Especially suitable alkylamines are the secondary and tertiary alkylamines of the formula $(R')_2NH$ and $(R')_3N$. The alkyl groups ($R'$) of these secondary or tertiary alkylamines preferably will contain from 1 to about 10 carbon atoms, most desirably less than 6 carbon atoms with a highly preferred selection being that each $R'$ group contain from 1 to 3 carbon atoms, that is, for example, methyl, ethyl, propyl. Most desirably the amine will be a secondary amine, for example, dimethylamine or diethylamine. The tertiary-alkyl alcohols contemplated for use herein are the tertiary monohydric alkyl alcohols having from 4 to 8 carbon atoms in the tertiary alkyl group thereof, e.g., t-butanol, t-pentanol (t-amyl alcohol), t-heptanols, t-hexanols. Preferably, the tertiary-alkyl alcohol will be tertiary butanol or tertiary pentanol, commonly referred to as tertiary amyl alcohol. The anhydrous, inert organic diluent employed herein will be routinely selected by those skilled in the art and is employed as a convenient carrier in which to allow the reaction to take place. Exemplary of these diluents are those materials commonly considered in the chemical industries as chemical solvents and which include both aliphatic, or acyclic, materials and cyclic materials. The cyclic organic compounds include the homocyclic organic solvents, both alicyclic and aromatic. The preferred solvents are the aliphatic, alicyclic or aromatic hydrocarbons, e.g., the hydrocarbons containing from 6 to 9 carbon atoms. Exemplary of the preferred materials are the aliphatic hexanes, heptanes, octanes, nonanes, etc., as well as the alicyclic forms thereof, and representative of the aromatic compounds are benzene and toluene and xylene. The diluent employed should be inert, that is, it should not react with any of the ingredients employed, or formed, and for reasons indicated hereinafter it should be anhydrous. The amount of the diluent employed may vary over a wide range with the amount generally being selected so as to provide a consistency in the reaction medium which is capable of being generally, easily stirred. Suitable amounts will be those producing a solution concentration of the final product in the diluent of about 5 to about 15 weight percent. Additionally, it will be found quite convenient to add the alkylamine and the tertiary alkyl alcohol into the reactor employed as a solution in the diluent.

The amount of stannic halide, alkylamine and tertiary alkyl alcohol employed will be such that there is at least a stoichiometric amount of the alkylamine relative to the tin tetrahalide and also at least a stoichiometric amount of the tertiary-alkyl alcohol relative to the amount of tin tetrahalide employed. That is, the molar ratio of the amount of total alkylamine employed to the amount of tin tetrahalide employed will be, at least, about 4:1 and the total amount of tertiary alkyl alcohol employed, relative to the amount of tin tetrahalide employed, will likewise be, at least, 4:1. Preferably a stoichiometric excess will be employed, that is, it will be in excess of a molar ratio of about 4:1. Suitable results will be obtained by employing molar ratios of alkylamine to tin halide in the range of about 4.05:1 to about 4.6:1 with the ratio of the tertiary alkyl alcohol to tin tetrahalide also being in a range of about 4.05:1 to about 4.6:1.

In passing, it should be mentioned that the process involved herein includes hydrolytically sensitive materials viz. the starting tin tetrahalide, for example tin tetrachloride, as well as the final product, tin tetra(tertiary-alkoxide). Thus, it will be readily apparent to those skilled in the art that techniques should be employed which are conventional when employing, reacting and forming hydrolytically sensitive materials. That is, the process should be performed under anhydrous conditions and care should be taken to minimize the contact of the involved materials to water, for example, the water vapor of ambient air, otherwise low yields will result.

The present process may be looked upon as a sequential performance of two reaction steps followed by the isolation of the desired compound of the formula $Sn(OR)_4$, wherein R is a tertiary-alkyl group containing from 4 to 8 carbon atoms and preferably is a tertiary amyl or tertiary butyl group. The first two sequential steps may be viewed upon as the reaction of the alkylamine with the stannic halide so as to form an alkylaminestannic halide reaction product and then that reaction product reacts with a tertiary alkyl alcohol so as to form the desired compound and an amine hydrohalide by-product. As will be seen herein, the desired reactions can be effected employing different orders of addition. For example, all of the amine can first be added to the stannic tetrahalide to obtain the desired reaction, followed by the addition of the requisite amount of a tertiaryalkyl alcohol, or, if desired, only a portion of the requisite amount of the alkylamine can be added first with the remainder of the alkylamine being added at a later time, as with the addition of the tertiary-alkyl alcohol, for example, in admixture with the tertiary alkyl alcohol. Generally, it may be stated, however, that the requisite total amount of the alkylamine, that is, at least the stoichiometric amount, as indicated hereinbefore, will be added to the system, e.g. to the reaction product of the tin tetrahalide and alkylamine resulting from the addition of a first portion, substantially no later than the completion of the addition of the tertiary-alkyl alcohol. The reason for this, and what is meant by that terminology, is to avoid the possibility of the tertiary-alkyl alcohol having an opportunity to react with halide moieties which have not been deactivated by reaction with the alkylamine; thus, the total requisite amount of the alkylamine will be introduced into the system sufficiently early so as to substantially preclude any significant and adverse decrease in yield of the desired product which may result by having a temporary deficiency of alkylamine in the reactor. If the addition of the alkylamine is split, i.e., it is added generally at two different points in time, it will generally be found quite convenient to add as a first portion a sufficient amount of the alkylamine so as to provide a molar ratio to tin tetrahalide of at least about 2:1; the remainder of the charge then being subsequently added such as for example, in admixture, with the tertiary alcohol. For example, if the total charge of alkylamine is to be in a molar ratio of at least about 4.05:1, relative to the tin halide, the alkyl alcohol may first be added in an amount sufficient to provide about 2 moles of the alkylamine per mole of stannic chloride with the remainder of at least 2.05 moles of alkylamine per mole of stannic chloride being subsequently added. If it is desired to initially add only a portion of the alkylamine and then to subsequently add the remainder, routine experiments will readily and quickly determine the optimum ratios of how the alkylamine should be split for the particular system involved. Generally, however, as previously indicated, it will be found convenient to split the addition so as to initially add a sufficient amount so as to provide a mole ratio of at least about 2:1 with the remainder being subsequently added. From a capital investment point of view, and from a total operational point of view, it will be most convenient, however, to simply first add all of the alkylamine, and then follow this by the addition and reaction of the tertiary-alkyl alcohol with the formed alkylamine-stannic halide reaction product.

The reaction of the stannic halide, for example, tin tetrachloride and the alkylamine is substantially instantaneous and results in an exothermic reaction. It is generally preferred to employ cooling during this reaction to keep the temperature less than about 30°C. such as, for example, between about 10° to 30°C. with quite suitable results being obtained by using temperatures ranging from about 15° to about 25°C. Suitable agitation should be employed during the process. The reaction of the alkylamine and tin tetrahalide results in the formation of a tin tetrahalide-alkylamine reaction product which is a solid and which becomes dispersed in the organic diluent. This solid reaction product is then a reactant with the tertiary-alkyl alcohol which reaction results in the formation of an amine hydrohalide by-product and the desired tin tetra(tertiary-alkoxide). The tin tetra(tertiary alkoxide) is in solution with the organic diluent and the amine hydrohalide exists as an insoluble solid by-product. Thus, all that is required is the addition of the tertiary alkyl alcohol to the alkylamine-stannic halide reaction product and then reacting same so as to form the amine hydrohalide and the stannic tertiary alkoxide. This latter reaction is likewise, preferably, carried out with stirring inasmuch as it will be appreciated that this will facilitate the reaction of the solid alkylamine-stannic halide reaction product with the alcohol. Generally, it is preferred to maintain the temperature again in the range of about 10° to 30°C, for example, 15° or 20° to about 25°C and to stir the system at least about 2 or 3 hours after the addition of the tertiary alcohol had been completed. If it is desired to check the reaction to insure that it is substantially complete it is possible to remove aliquot portions of the solid which forms, i.e., the amine hydrohalide, wash it and then add water to it; if the solid material is substantially all amine hydrohalide a solution will result. But if, however, the solid material still represents some of the alkylamine-stannic halide reaction product, a precipitate will result.

Following the reaction wherein the amine hydrohalide forms as a dispersion in the solution containing the desired tin tetra(tertiary-alkoxide) all that is required is the isolation, or separation, of the desired product therefrom. Conventional techniques may be employed in this regard. For example, it will be found to be quite convenient to simply remove the amine hydrohalide by filtration, for example, vacuum filtration, and then to isolate the desired product from the filtrate. Of course, sound practices recommend that the filter cake be washed to remove all residual product left in the filter cake. The filtrate is then preferably heated under vacuum so as to distill off and evaporate the organic diluent leaving behind a residue of the desired product. It will generally be quite convenient to effect this evaporation under vacuum, for example, at a pressure of 10–20 millimeters of mercury using conventional equipment e.g., rotary vacuum evaporators. The residual product is then similarly separated, preferably by distilling under high vacuum, for example, at less than a millimeter of mercury, typically one-tenth of a millimeter or less, at the dominant boiling point of the product at that pressure. In passing, it should be mentioned that it is believed that a reaction takes place between the by-product amine hydrohalide and the desired tin alkoxide product. Accordingly, sound practices will be employed to minimize the opportunity for such reactions. That is, prolonged setting of the final reacted system should not be allowed and the heating employed in isolating the desired product will preferably be at as low a temperature as reasonably possible in case small amounts of the by-product have found their way into the final product notwithstanding their removal, for example, by filtration.

While the above describes the present invention with sufficient particularity to enable those skilled in the art to make and use same, nonetheless, a few examples follow which further exemplify the present invention. As indicated above some of the materials involved are generally, highly hydrolytically sensitive and, accordingly, in practicing the examples, and the invention, care should be taken to minimize the exposure of these materials to water, particularly the water vapor existing in the ambient atmosphere so as to maintain yields at a maximum. In general, it has been found quite convenient to dry the equipment to be employed and especially the reactor flask in heated air prior to utilization. Additionally, it will be found quite convenient to maintain a nitrogen atmosphere, or other inert atmosphere, over the reaction to further eliminate possible contact with water. Additionally, during the employed filtration step care should be taken to minimize, insofar as possible, contact with ambient humid air; one suitable technique which will be found to be quite convenient is that, in vacuum filtering, for example by employing a porous filter, an elastomeric film or membrane be employed over the filtration apparatus so as to function in the manner of a diaphragm. Finally, it will also be found desirable to dry the materials prior to utilization. Conveniently, drying for several days over molecular sieves, for example, a Linde type 3A molecular sieve is suitable.

EXAMPLE I

Into a dry reactor flask was added 130 grams of tin tetrachloride and 1,000 ml of normal heptane. With cooling, so as to maintain a temperature of about 15° to about 20°C, and with stirring there was then added to the tin tetrachloride solution a solution of about 165 grams of diethylamine dissolved in 200 ml of normal heptane. It was observed that after the addition of part of the diethylamine i.e., at about the point where the molar ratio of added diethylamine to tin tetrachloride was about 2:1, there was a substantial subsiding of the exotherm. After completion of the addition of the diethylamine the contents were stirred for several minutes and at this point there was a slurry, or dispersion, of a tin chloride-alkylamine reaction product in the heptane diluent.

About 203 grams of tertiary-amyl alcohol was then added with stirring and with the temperature being maintained at about 15°–20°C. There then resulted a thick precipitate which was somewhat difficult to stir and more heptane (500 ml) was added to obtain a more fluid consistency capable of being more easily stirred. The reactor contents were left overnight at room temperature with stirring. The product was a dispersion of a solid amine hydrochloride dispersed in a solution of tin tetra(tertiary-amyl oxide) dissolved in the heptane diluent. The solid amine hydrochloride was then vacuum filtered and the filter cake washed twice with 150 ml of heptane. The filtrate and the washings were then evaporated under vacuum, at a pressure of about 10 to about 20 milliliters of mercury, to separate the heptane diluent therefrom. The residue was then distilled at a pressure of about 0.09 milliliters of mercury and at a temperature of about 92°C to isolate the tin tetra(tertiary-amyl oxide). A yield of 82% of the product resulted.

EXAMPLE II

The general procedure of Example I was followed with the charge being about 130 grams of tin tetrachloride and about 1000 ml of benzene. About 170 grams of diethylamine, in about 150 ml of benzene, was then added over a period of 30 minutes with stirring and with the temperature being maintained at about 20°C. About 205 grams of tertiary-amyl alcohol, dissolved in about 200 ml of benzene, was then added to the dispersion with the temperature being maintained about 20°C. An additional quantity of benzene (about 500 ml) was added to maintain fluidity at a more convenient point for stirring. The reacted system, i.e. dispersion, was then filtered, washed, and the benzene separated in the manner indicated in Example I. The resulting liquid residue of tin tetra(tertiary-amyl oxide) product contained a small amount of a crystalline precipitate, presumably diethylamine hydrochloride, which was removed by filtration prior to distillation of the final product. The tin tetra(tertiary-amyl oxide) was recovered in a 79% yield.

EXAMPLE III

The procedure of Example I is generally followed with the exception that the diethylamine is first added in an amount to produce a molar ratio of about 2:1 of the amine to the tin tetrachloride. To the resulting dispersion the remainder of the amine, along with the 203 grams of tertiary amyl alcohol, as an admixture in heptane, is subsequently added.

The yield is generally about the same as that of Example I, indicating that all of the amine need not be added prior to the addition of the tertiary alcohol.

EXAMPLE IV

The general procedure of Example I was followed with about 225 grams of triethylamine (dissolved in about 150 ml of heptane) being added to a solution of about 130 grams of tin tetrachloride dissolved in about 1200 ml of heptane. The addition was done with stirring and cooling to maintain a temperature between about 20° and 25°C. resulting in the formation of a brownish tin tetrachloride-alkylamine reaction product precipitate dispersed in the heptane diluent. About 205 grams of tertiary amyl alcohol, in 150 ml of heptane, was added with stirring and cooling to maintain a temperature of about 20°C. The contents were allowed to set overnight with stirring at room temperature after which vacuum filtration followed. The filter cake was washed twice using 150 ml of heptane each time. The filtrate and the washings were then evaporated under vacuum to separate the heptane diluent and the residue distilled under vacuum to give a yellow liquid tin tetra(-tertiary-amyl oxide) product. The yield was about 40% (boiling point about 95°C. at about 0.1 milliliters of mercury).

EXAMPLE V

The procedure of Example I was followed with the exception that the diethylamine was not added first as in Example I. That is, the diethylamine and the tertiary-amyl alcohol were first combined with about 200 ml of heptane and this admixture then added to the stannic chloride solution. This resulted in a 24% yield of product and it was observed that a considerable amount of a solid co-distilled during the distillation of the tin tetra(tertiary-amyl oxide). This example illustrates the benefits of first adding at least a portion of the alkylamine.

EXAMPLE VI

Ammonia gas was bubbled into a solution of tin tetrachloride (130 grams) in heptane (1000 ml) with stirring and cooling; the mixture became quite thick after about 15 minutes and an additional amount (500 ml) of heptane was added to increase the fluidity. The temperature was maintained at about 20°C. After about 40 minutes of gas passage the mixture appeared saturated with ammonia and a white solid dispersed in heptane was obtained. Tertiary-amyl alcohol (205 g.) in heptane (100 ml) was then added with the passage of ammonia gas continued, although at a slightly reduced rate, and the temperature maintained at about 20°C; after the addition of the tertiary-amyl alcohol, the resulting dispersion was fluid and was stirred at room temperature overnight. The solids were separated by vacuum filtration and the filter cake washed twice using about 200 ml of heptane each time. The filtrate and washings were evaporated under vacuum but only a trace of oily liquid remained; the yield of tin tetra(tertiary-amyl oxide) using this ammonia addition was virtually zero.

EXAMPLE VII

The procedure of Example I and VI were generally followed with monomethylamine gas being employed instead of ammonia and with the initial charge being about 130 grams of tin tetrachloride in about 1400 ml of heptane. Additionally, the tertiary-amyl alcohol was added in about 200 ml of heptane. No tin tetra(tertiary-amyl oxide) was recovered.

As will be readily apparent to those skilled in the art, the present method may be used to make other alkoxides of tin and, likewise, may be employed to produce other metal alkoxides, especially tertiary alkoxides.

Having described the invention above, it will, of course, be apparent that modifications are possible which do not depart from the spirit and scope thereof.

I claim:

1. An anhydrous process for producing a compound of the formula $Sn(OR)_4$, wherein R is a tertiary alkyl group containing from 4 to 8 carbon atoms, which comprises: reacting a tertiary alkyl alcohol, wherein the alkyl group contains from 4 to 8 carbon atoms, with a stannic tetrahalide-alkylamine reaction product in the presence of an inert anhydrous organic diluent so as to form a dispersion of a solid amine hydrohalide in a solution containing said compound, said alkylamine being a secondary or tertiary alkylamine wherein each alkyl group thereof contains up to 10 carbon atoms; and isolating said compound from said dispersion.

2. The process of claim 1 wherein said tertiary alkyl alcohol is tertiary amyl alcohol and wherein said stannic tetrahalide-alkylamine reaction product is the reaction product of at least 4 moles of said amine per mole of said stannic halide and wherein each alkyl group of said alkylamine contains 6 carbon atoms or less.

3. An anhydrous process for producing a stannic tertiary-alkoxide, wherein at least about 4 moles of an alkylamine and at least about 4 moles of a tertiary alcohol are employed as reagents per mole of a stannic tetrahalide, said process comprising: reactively combining at least a portion of said alkylamine, wherein said amine is a secondary or tertiary alkylamine having up to 10 carbon atoms in each alkyl group thereof, with said stannic tetrahalide so as to form a reaction product thereof; adding to said reaction product a tertiary alkyl alcohol having from 4 to 8 carbon atoms and reacting same so as to form an amine hydrohalide and said stannic tertiary-alkoxide and, wherein the remainder, if any, of said amine is added to said reaction product substantially no later than the completion of the addition of said tertiary alkyl alcohol; and isolating said stannic tertiary-alkoxide.

4. The process of claim 3 wherein said isolating comprises filtering to remove said amine hydrohalide and heating the filtrate so as to recover said stannic tertiary-alkoxide.

5. The process of claim 3 wherein said amine contains 6 carbon atoms or less in each alkyl group thereof.

6. The process of claim 5 wherein each alkyl group of said alkylamine contains from 1 to 3 carbon atoms.

7. The process of claim 6 wherein said portion of said alkylamine is an amount sufficient to provide at least about 2 moles of said amine per mole of stannic halide.

8. The process of claim 7 wherein said halide is a chloride.

9. The process of claim 6 wherein said tertiary alcohol is tertiary-butyl or tertiary-pentyl alcohol.

10. The process of claim 9 wherein said amine is dimethylamine or diethylamine.

11. The process of claim 8 wherein all of said amine is first reacted with said stannic tetrachloride.

12. An anhydrous process for forming a compound of the formula $Sn(OR)_4$ wherein R is a tertiary alkyl group containing 4 to 8 carbon atoms which comprises: reacting a stannic tetrahalide with a secondary or tertiary alkylamine in an anhydrous inert organic diluent, wherein each alkyl group of said amine contains between 1 and 10 carbon atoms and wherein the molar ratio of said amine to said stannic halide is at least about 4:1, so as to form a dispersion of an alkylamine-stannic halide reaction product; reacting a tertiary alkyl alcohol, wherein the alkyl group contains 4 to 8 carbon atoms, with said dispersion of said reaction product in a molar ratio of at least about 4:1, based on said stannic tetrahalide, so as to form an amine hydrohalide solid reaction product and said compound; and isolating said compound.

13. The process of claim 12 wherein said isolating comprises removing said amine hydrochloride by filtration and evaporating said organic diluent from the filtrate.

14. The process of claim 12 wherein each alkyl group of said alkylamine contains 6 carbon atoms or less.

15. The process of claim 14 wherein each of said alkyl groups of said amine contains between 1 and 3 carbon atoms.

16. The process of claim 13 wherein said tertiary alkyl alcohol is tertiary-butyl or tertiary-amyl alcohol.

17. The process of claim 12 wherein the molar ratio of said amine to said stannic halide is between about 4.05 to about 4.6:1 and wherein the ratio of tertiary alkyl alcohol to said stannic halide is between about 4.05 to about 4.6:1

18. An anhydrous process for producing tin tetra(tertiary-butoxide) or tin tetra(tertiary-pentoxide) using stannic tetrachloride, diethylamine and tertiary-pentanol or tertiary-butanol with the respective amounts of said pentanol or said butanol and the amount of said diethylamine being in a molar ratio to said stannic tetrachloride of at least about 4:1 said process comprising: reacting at least a portion of said diethylamine with said stannic chloride in the presence of an inert, anhydrous, organic diluent so as to form a reaction product; adding said pentanol or said butanol to said reaction product and reacting same so as to form a dispersion of an amine hydrochloride in a solution containing said tin butoxide or said tin pentoxide, wherein the remainder of said diethylamine, if any, is added to said reaction product substantially no later than the completion of the addition of said butanol or said pentanol; separating said amine hydrochloride from said dispersion and recovering said tin butoxide or said tin pentoxide from said solution.

19. The process of claim 18 wherein said portion is an amount sufficient to provide about 2 moles of diethylamine per mole of stannic chloride and a remainder of at least about 2.05 moles of diethylamine per mole of stannic chloride is added in admixture with said pentanol or butanol.

20. The process of claim 18 wherein said portion is an amount to provide at least about 2 moles of said amine per mole of stannic alkoxide.

21. The process of claim 20, wherein all of said amine is first reacted with said stannic chloride.

* * * * *